(12) United States Patent
Durand et al.

(10) Patent No.: US 9,980,645 B1
(45) Date of Patent: May 29, 2018

(54) HIGH-CONTACT DENSITY ELECTRODE AND FABRICATION TECHNIQUE FOR AN IMPLANTABLE CUFF DESIGN

(75) Inventors: Dominique M. Durand, Solon, OH (US); Brian Wodlinger, Pittsburgh, PA (US)

(73) Assignee: Case Western Reserve University, Cleveland, OH (US)

( * ) Notice: Subject to any disclaimer, the term of this patent is extended or adjusted under 35 U.S.C. 154(b) by 1459 days.

(21) Appl. No.: 13/529,514

(22) Filed: Jun. 21, 2012

Related U.S. Application Data (60) Provisional application No. 61/571,129, filed on Jun. 21, 2011.

(51) Int. Cl.
*A61B 5/103* (2006.01)
*A61B 5/117* (2016.01)
*A61B 5/00* (2006.01)
*A61N 1/05* (2006.01)

(52) U.S. Cl.
CPC .............. *A61B 5/00* (2013.01); *A61N 1/0556* (2013.01)

(58) Field of Classification Search
CPC ........................................................ A61B 5/00
USPC ................................. 600/587, 595; 607/118
See application file for complete search history.

(56) References Cited

U.S. PATENT DOCUMENTS

| 5,038,781 A * | 8/1991 | Lynch | A61N 1/36003 |
| | | | 607/48 |
| 6,587,725 B1 * | 7/2003 | Durand | A61N 1/3601 |
| | | | 607/118 |
| 2005/0251221 A1 * | 11/2005 | Zdravkovic | A61N 1/0551 |
| | | | 607/46 |
| 2006/0004286 A1 * | 1/2006 | Chang | A61B 5/06 |
| | | | 600/435 |
| 2007/0112404 A1 * | 5/2007 | Mann | A61N 1/0551 |
| | | | 607/116 |
| 2007/0142862 A1 * | 6/2007 | DiLorenzo | A61N 1/3605 |
| | | | 607/2 |
| 2007/0161919 A1 * | 7/2007 | DiLorenzo | A61B 5/04001 |
| | | | 600/544 |

(Continued)

OTHER PUBLICATIONS

Hess, A.E. et al., "Development of a Microfabricated Flat Interface Nerve Electrode Based on Liquid Crystal Polymer and Polynorbornene Multilayered Structures," Proceedings of the 3rd International IEEE EMBS Conference on Neural Engineering, Kohala Coast, Hawaii, May 2-5, 2007, pp. 32-35.

(Continued)

*Primary Examiner* — May Abouelela
(74) *Attorney, Agent, or Firm* — Tarolli, Sundheim, Covell & Tummino LLP (57) ABSTRACT

A method and an electrode for monitoring electrical activity in a nerve are provided along with a method of fabricating such an electrode. The electrode includes a cuff formed from a chronically-implantable material that, when implanted, extends at least partially around an external periphery of the nerve. A plurality of contacts are supported by the cuff to be arranged adjacent to different regions of the nerve distributed along a transverse direction of the nerve when the cuff is implanted. A multiplexer is coupled to the cuff to be implanted for receiving electrical signals introduced to the contacts by the nerve and multiplexing, in vivo, the electrical signals to be transmitted to an external receiver over a shared communication channel.

11 Claims, 5 Drawing Sheets

(56) References Cited

U.S. PATENT DOCUMENTS

| | | | | |
|---|---|---|---|---|
| 2007/0239243 | A1* | 10/2007 | Moffitt | A61N 1/0556 607/118 |
| 2009/0292345 | A1* | 11/2009 | Triantis | A61B 5/04001 607/118 |
| 2010/0191303 | A1* | 7/2010 | Kieval | A61B 5/02028 607/44 |
| 2010/0241207 | A1* | 9/2010 | Bluger | A61B 5/0422 607/118 |
| 2010/0305664 | A1* | 12/2010 | Wingeier | A61N 1/3605 607/62 |
| 2010/0305674 | A1* | 12/2010 | Zarembo | A61N 1/0556 607/118 |
| 2010/0312320 | A1* | 12/2010 | Faltys | A61N 1/0556 607/118 |
| 2011/0060392 | A1* | 3/2011 | Zdeblick | A61N 1/37205 607/115 |
| 2011/0092842 | A1* | 4/2011 | Decaria | A61B 5/04001 600/544 |
| 2011/0172725 | A1* | 7/2011 | Wells | A61N 1/36017 607/3 |
| 2011/0202108 | A1* | 8/2011 | Gross | A61N 1/36007 607/46 |
| 2011/0230943 | A1* | 9/2011 | Johnson | A61N 1/05 607/116 |
| 2011/0301658 | A1* | 12/2011 | Yoo | A61N 1/36167 607/9 |
| 2012/0022347 | A1* | 1/2012 | Liu | A61B 5/0488 600/316 |
| 2014/0288620 | A1* | 9/2014 | DiLorenzo | A61N 1/36053 607/62 |

OTHER PUBLICATIONS

Riso, R.R. et al., "Nerve Cuff Recordings of Muscle Afferent Activity from Tibial and Peroneal Nerves in Rabbit During Passive Ankle Motion," IEEE Transactions on Rehabilitation Engineering, vol. 8, No. 2, Jun. 2000, pp. 244-258.

Suaning, G.J. et al., "Microelectronic Retinal Prosthesis: III. A New Method for Fabrication of High-Density Hermetic Feedthroughs," Proceedings of the 28th IEEE EMBS Annual International Conference, New York, New York, Aug. 30-Sep. 3, 2006, pp. 1638-1641.

Suaning, G.J. et al., "Fabrication of multi-layer, high-density microelectrode arrays for neural stimulation and bio-signal recording," Proceedings of the 3rd International IEEE EMBS Conference on Neural Engineering, Kohala Coast, Hawaii, May 2-5, 2007, pp. 5-8.

Tesfayesus, W. and Durand, D.M., "Blind source separation of peripheral nerve recordings," Journal of Neural Engineering, vol. 4, 2007, pp. S157-S167.

Wodlinger, B. and Durand, D.M., "Localization and Recovery of Peripheral Neural Sources with Beamforming Algorithms," IEEE Transactions on Neural Systems and Rehabilitation Engineering, vol. 17, No. 5, Oct. 2009, pp. 461-468.

Zariffa, J. and Popovic, M.R., "Application of EEG Source Localization Algorithms to the Monitoring of Active Pathways in Peripheral Nerves," 30th Annual International IEEE EMBS Conference, Vancouver, Canada, Aug. 20-24, 2008, pp. 4216-4219.

Zariffa, J. and Popovic, M.R., "Solution space reduction in the peripheral nerve source localization problem using forward field similarities," Journal of Neural Engineering, vol. 5, 2008, pp. 191-202.

* cited by examiner

HIGH-CONTACT DENSITY ELECTRODE AND FABRICATION TECHNIQUE FOR AN IMPLANTABLE CUFF DESIGN

CROSS-REFERENCE TO RELATED APPLICATIONS

This application claims the benefit of U.S. Provisional Application No. 61/571,129, filed Jun. 21, 2011, which is incorporated in its entirety herein by reference.

GOVERNMENT LICENSE RIGHTS

This invention was made with government support under Grant No. 2R01-Ns 032845-10 awarded by the National Institute of Health. The government has certain rights in the invention.

BACKGROUND OF THE INVENTION

1. Field of the Invention

This application relates generally to a method and apparatus for monitoring electrical signals conducted by a nerve and, more specifically, to an in-vivo nerve interface comprising an electrode array, a method of utilizing signals sensed by the electrode array to control a prosthetic device, and a method of fabricating the electrode array.

2. Description of Related Art

Despite great advances in many areas of medical technology, the challenge of providing amputees with a prosthetic limb having the intuitive control and functionality of a natural limb remains. Improvements in materials have made prosthetics lighter and stronger, but little headway has been made in improving the functionality and control over the prosthetics by amputees. In an effort to improve the functionality and control of prosthetics attempts have been made to utilize electrical control signals from the muscles of the residual limb. While such techniques may hold future promise they have, thus far, not proven to be sufficiently robust and lack the use of intuitive control signals that would allow the amputee to take advantage of a dexterous prosthetic.

A more-recent goal in designing prosthetics is to give amputees more functionality, ideally approaching the level of functionality afforded by the limbs the prosthetics are to replace. Enabling an amputee to effectively utilize and control a prosthetic limb with so many degrees of freedom requires the prosthetic to respond to the numerous control signals used by the human body that would otherwise control the limb replaced by the prosthetic. Interfacing with the amputee's nervous system provides the opportunity to sense movement intention directly, affording the amputee natural, volitional control of the prosthetic. Attempts at decoding the amputees' intentions in controlling a prosthetic directly from the brain have involved the use of electroencephalograms recorded from the surface of the scalp, and penetrating cortical arrays. But since so many bodily control signals are transmitted by the brain it is difficult to isolate the signals intended to control a prosthetic from others that are intended control another of the amputee's remaining limbs.

Other nerve interfaces have utilized a plurality of needle-like protrusions that are each surgically inserted into individual nerve fibers included in a nerve bundle. Each inserted protrusion acts as a contact that directly senses the signal transmitted by its respective nerve fiber, and is connected to its own dedicated wire that transmits the sensed signals externally of the amputee to a prosthetic controller. Such an interface is invasive, exposing the affected nerve fibers to damage from the surgical procedure to insert the protrusions. Further damage to the nerve is also possible due to the tethering forces required necessarily exerted on the nerve to support a large number of wires corresponding to the number of individual protrusions.

BRIEF SUMMARY OF THE INVENTION

Accordingly, there is a need in the art for a method and apparatus for monitoring electrical activity in a nerve. Such a method and apparatus can discriminate between electrical signals conducted by different regions of the nerve, be robust, and minimize forces imparted on the nerve to ensure the relationship between the apparatus and nerve is maintained.

According to one aspect, the subject application involves an electrode for monitoring electrical activity in different regions of a nerve. The electrode includes a cuff formed from a chronically-implantable material that, when implanted, extends at least partially around an external periphery of the nerve. Two or more contacts are supported by the cuff to be arranged adjacent to the different regions of the nerve along a transverse direction of the nerve when the cuff is implanted. A multiplexer is coupled to the cuff to be implanted for receiving electrical signals introduced to the contacts by the nerve and multiplexing, in vivo, the electrical signals to be transmitted to an external receiver over a shared communication channel.

According to another aspect, the subject application involves a method of monitoring electrical activity in a nerve of a subject. The method includes receiving electrical signals introduced to a plurality of contacts chronically implanted in the subject and arranged adjacent to different regions of an exterior periphery of the nerve. The signals introduced are manipulated, within the subject, for transmission over a common communication channel that is shared for transmission of the electrical signals introduced to each of the contacts. After the manipulation occurs, the manipulated signals are transmitted over the common communication channel to be received by a receiver that controls operation of a prosthetic device being worn by the subject.

According to another aspect, the subject application involves a method of fabricating an electrode for monitoring electrical activity along a nerve. The method includes arranging a plurality of insulated wires into substantially parallel arrangement with each other. Each of the insulated wires includes an electrical conductor, which can optionally be a stranded conductor, protected by an insulating material. The separation between the electrical conductor provided to a first insulated and the electrical conductor provided to a second insulated wire, which is immediately-adjacent to the first insulated wire, is limited to a distance established by the insulating material provided to the first and second insulated wires. The insulated wires are then heated to fuse the insulating material provided to the first and second insulated wires together. An aperture is formed in the insulating material provided to each of the insulated wires to expose a portion of each electrical conductor and form a contact for introducing an electrical signal conducted by the nerve to the electrical conductor.

According to another aspect, the subject application involves method of mitigating an effect of an external stimulation on electrical activity monitored along a nerve of a subject. The method according to this aspect includes, with an electrode implanted in the subject, receiving an instruction that an electrical signal is to be introduced to a target region of the nerve as the external stimulation. Signals introduced to the plurality of contacts provided to the electrode are received from different regions of the nerve at a time other than when the electrical signal is to be introduced to the target region. Within the subject, the received signals are manipulated to prepare information represented by the received signals for transmission over a common, shared communication channel. The method also includes interfering with consideration of another signal introduced to the plurality of contacts at a time when the electrical activity along the nerve is affected by the external stimulation during the manipulation. The information represented by the plurality of signals is transmitted over a common, shared communication channel to be received by a receiver, which can optionally be an external receiver.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Figure 1:
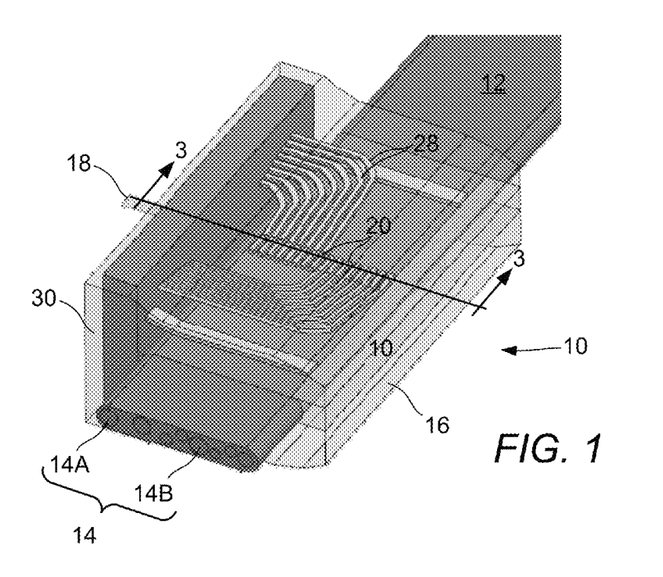
FIG. 1 shows a first perspective view of an illustrative embodiment of an electrode implanted in a residual limb and coupled to a nerve.

FIG. 1 shows an illustrative embodiment of an electrode 10 for monitoring electrical activity along a nerve 12, which is schematically depicted and partially cutaway in FIG. 1 for illustrative purposes. The nerve 12 conducts electrical signals from the brain through different regions, referred to generally at 14, to control movements of a person's limbs. Thus, electrical signals conducted through a first region 14A may control finger movement while electrical signals conducted through a second region 14B may control wrist articulation, for example.

As shown in FIG. 1, the electrode 10 includes a cuff 16, which can optionally be in the form of an elongated band, that is chronically implantable in a person to extend at least partially, and optionally entirely, about an external periphery of the nerve 12. Rather than causing a portion of the contacts 20 to protrude into an interior of the nerve 12, the contacts 20 can optionally all be arranged adjacent to different exterior regions spaced apart in a transverse direction of the nerve. The cuff 16 extends a suitable extent about the nerve 12, when implanted, to interfere with separation of the cuff 12 from the nerve 12 when subjected to forces urging the cuff 16 away from the nerve 12 under normal usage. For instance, a plurality (four (4) in the illustrative embodiment shown in FIGS. 1 and 2) wires 18 extend outwardly from the electrode 10 to facilitate communications between the electrode 10 and external devices as described below. Such wires 18 may be suspended from the electrode 10 or may otherwise exert forces on the electrode 10 when a residual limb in which the nerve 12 is located is moved.

The cuff 16 is said to be chronically implantable to couple the electrode 10 to the nerve 12. Chronic implantation requires a surgical procedure to be performed to install the cuff 16 on the nerve 12 and remove the cuff 16 from the nerve 12. In other words, to be considered chronic the implantation of the electrode 10 must be a long-term solution instead of a temporary implantation, where a target removal date is anticipated when a medical condition subsides.

As a chronically-implantable device, the cuff 16 can be formed from a material that is generally inert to substances likely to be encountered within a human body. Such a material can optionally be approved by a regulatory body such as the U.S. Food and Drug Administration ("FDA") for implantation, long term or at least short term, in a human body. Examples of such a material include, but are not limited to flexible and biocompatible materials such as: medical grade silicone, polyether ether ketone, polytetrafluoroethylene, poly(methyl methacrylate), polyethylene, and the like.

The cuff 16 can support a plurality of contacts 20 at locations where the contacts 20 will be arranged to sense electrical signals transmitted by a plurality of the different regions 14 of the nerve 12. The peripheral nervous system carries sensory and motor information that could be useful as command signals for function restoration in areas such as neural prosthetics and Functional Electrical Stimulation. The contacts 20 provide a robust interface for recording such electrical signals transmitted along the nerve 12.

Figure 2:
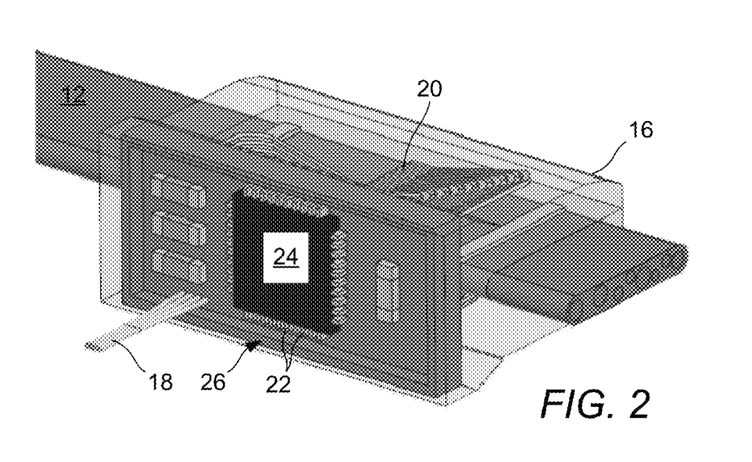
FIG. 2 shows a second perspective view of an illustrative embodiment of an electrode implanted in a residual limb and coupled to a nerve.

As shown in FIGS. 1 and 2, for example, the contacts 20 are to be positioned adjacent to the external periphery of the nerve 12, extending along a transverse direction of the nerve 12 when the cuff 16 is implanted. In such an arrangement the contacts 20 can sense electrical signals conducted by each of the various different regions 14A, 14B. The sensed electrical signals transmitted through the contacts 20 allow a recipient controller to distinguish, along the transverse direction, electrical signals sensed in the region 14A from electrical signals sensed in the region 14B based on which of the contact(s) 20 sensed the electrical signals, and optionally a quality such as the magnitude of the voltage and/or current of the electrical signal sensed by a plurality of the contacts 20.

Figure 3:
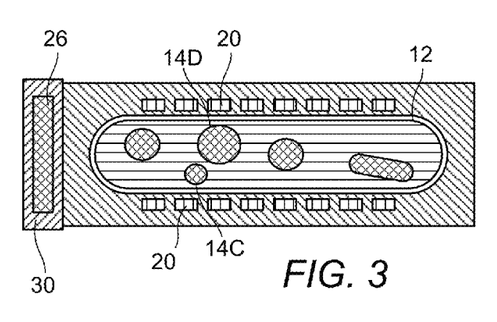
FIG. 3 shows a partially cutaway view taken along line 3-3 in FIG. 1.

Shown clearly in FIG. 3, the different regions 14 of the nerve 12 that conduct electrical signals to be sensed by the contacts 20 can be located at different vertical (according to the perspective shown in FIG. 3) locations within the nerve 12, as well as being distributed horizontally in the transverse direction. To distinguish between electrical signals conducted by a region 14C at a relatively-low elevation from electrical signals conducted by a region 14D at a relatively-high elevation, the contacts 20 can be supported by the cuff 16 to be positioned on opposite sides (e.g., above and below) of the nerve 12.

Referring once again to FIGS. 1 and 2, each contact 20 is operatively connected to an input terminal 22 of a processor 24 forming a portion of a control unit 26 that is supported by the cuff 16. An insulated wire 28 can be provided, and optionally dedicated to form a conductive pathway between each contact and a respective input terminal 22 to convey signals induced in the contacts 20 by electrical signals conducted by the nerve 12 to the processor 24. The insulated wires 28 can each include a stranded conductor formed from a plurality of corrosion-resistant wire filaments protected within a sheath formed of an electrically-insulating material. The corrosion resistance can be achieved through the use of materials such as a metal or metal alloy approved by the FDA for implantation, such as, platinum, gold, a steel alloy (commonly referred to as "stainless steel") having a chromium content sufficient to resist oxidation and other forms of corrosion within the human body, and the like. Each of the wire filaments can be wound together, and optionally braided or otherwise arranged into a desired patter within the insulating material to ensure electrical continuity between each of the wire filaments of an insulated wire 28. Although the conductive pathways are described herein as embodied by insulated wires 28 for purposes of describing the present technology, it is to be understood that printed conductive pathways formed by conventional lithographic techniques and conductive pathways formed from sheets of electrically-conductive materials are also encompassed by the present disclosure.

Signals induced in the contacts 20 by electrical signals transmitted through regions 14 of the nerve 12 are conducted to the processor 24, where the signals are manipulated before being transmitted to an external receiver. An electrical signal conducted by one of the regions 14 can induce a signal in at least one, and optionally a plurality of the contacts 20. At least one quality such as the magnitude of the voltage of the signal induced in the contacts 20 will be a function of the proximity of each contact 20 relative to the region 14 conducting the electrical signal. Accordingly, based on the contacts 20 in which the signal is induced and the relative properties (e.g., the voltage magnitude) of the signal induced in each contact 20, the region 14 through which the electrical signal was conducted can be determined.

The control unit 26 is chronically implantable, and is to be coupled to the nerve 12 by the cuff 16 to manipulate the signals induced by electrical signals conducted by the nerve 12 before the manipulated signals are transmitted to the external receiver. As such, the control unit 26 can be enclosed within, and optionally hermetically sealed by a housing 30 to protect circuitry forming the processor 24 from the elements within the environment in which the electrode 10 is implanted. The housing 30 can optionally be formed from same material used for the cuff 16, or can optionally be formed from any material approved for chronic implantation that isolates the circuitry of the control unit 26 from the ambient environment of the implantation site.

The external receiver to which the manipulated signals are to be transmitted from the control unit 26 can optionally translate those signals into commands for controlling a mechanized prosthetic device or paralyzed limbs. As such, the external receiver is to be disposed externally of the residual limb (e.g., outside the body) in which the electrode 10 is implanted, and can optionally be provided to the prosthetic device.

The processor 24 can be implemented as a hard-wired, dedicated arrangement of circuit components, as a computer processing component executing computer-executable instructions stored in a non-transitory computer-readable medium (e.g., solid-state flash memory, hard drive, etc. . . . ), or a combination thereof. The method of manipulation, performed in vivo by the implanted control unit 26, can also optionally be defined by computer-executable instructions stored in a non-transitory computer-readable medium.

Regardless of its configuration, the processor 24 is operable to receive the signals induced in the plurality of contacts 20 and manipulate, in vivo, the received signals for transmission of the information carried by the manipulated signals over a common, shared communication channel. Manipulation of the signals can involve multiplexing the received signals, time shifting the received signals, or otherwise processing the signals received by the processor 24. Such manipulation allows the information conveyed by each signal received from a plurality of the different contacts 20 to be transmitted to the external receiver over the same wire 18, the same wireless network, or other shared communication channel over which one or more signals indicative of electrical activity occurring at a plurality of different regions 14 of the nerve 12 is transmitted to the external receiver. The shared communication channel, whether a hard-wired connection via the wire(s) 18 or via a wireless network connection via an antenna and transmitter provided to the electrode 10, for example, is commonly used for each such transmission to minimize the number of dedicated connectors such as the wires 18 extending outwardly, away from the electrode 10. Additionally, the low-power signals induced in the contacts 20 by electrical activity in the different regions 14 of the nerve 12 can optionally be amplified before being manipulated to promote accurate communication of the received signals. After the signal manipulation occurs, the manipulated signal can be transmitted from the residual limb where the electrode 10 is implanted over the common communication channel to be received by the external receiver for controlling operation of a prosthetic device.

Figure 4:
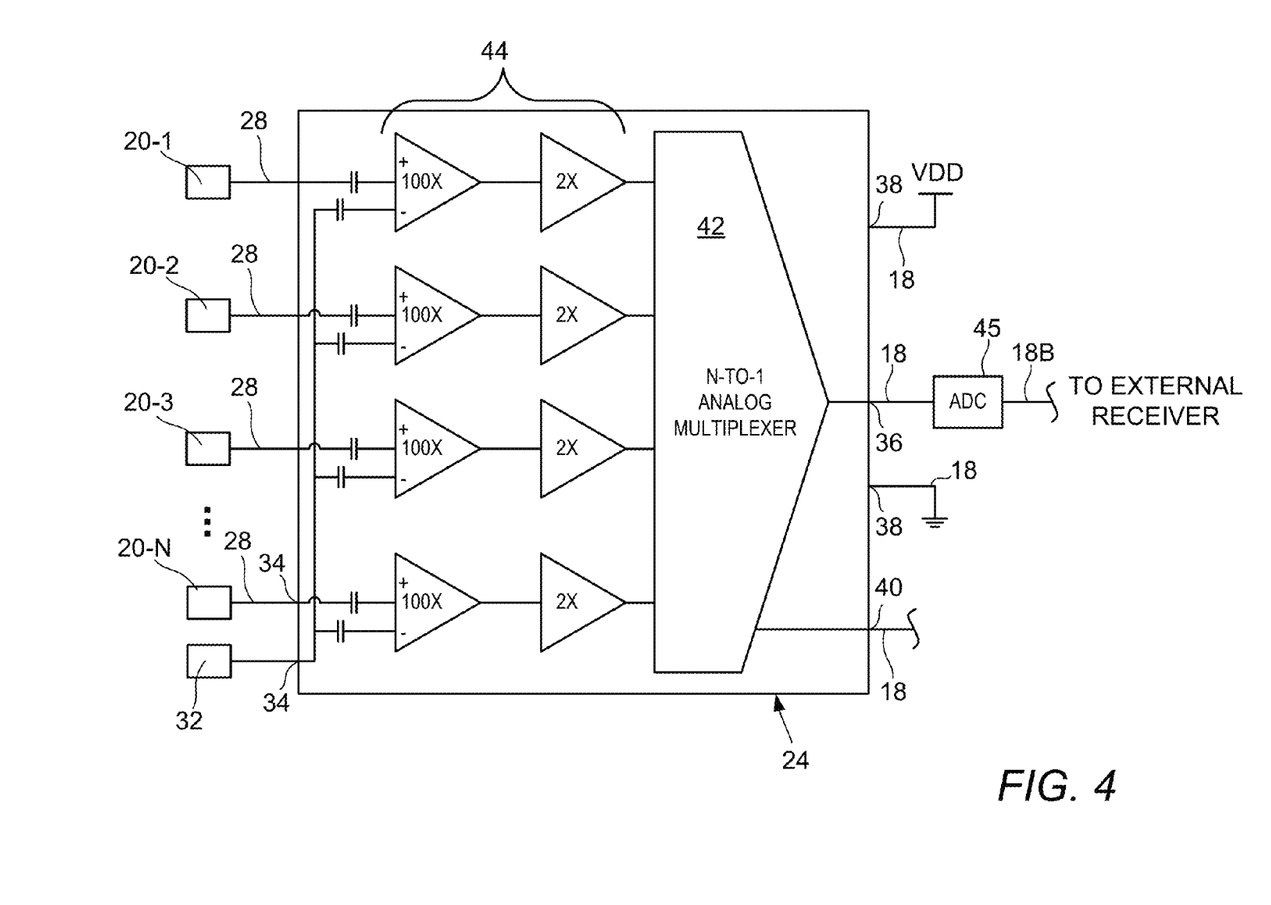
FIG. 4 shows a block diagram schematically depicting portions of a processor for manipulating signals to be transmitted over a shared communication channel to an external receiver.

An illustrative example of the processor 24 is represented by the functional block diagram of FIG. 4. For the embodiment shown, the plurality of different contacts 20 are individually referred to at 20-1, 20-2, 20-3, . . . 20-N, where N represents any desired integer number of contacts 20. Although at least four (4) contacts 20 are shown in FIG. 4 for illustrative purposes, it is to be understood that N can represent any desired number of contacts greater than or equal to two (2).

In addition to the contacts 20-1, 20-2, 20-3, . . . 20-N a reference contact 32 can be operatively connected to the processor 24 to provide a reference signal against which the signal received from each of the contacts 20-1, 20-2, 20-3, . . . 20-N for purposes of amplification. The reference contact 32 can span a significant portion (e.g., more than half the distance of the nerve 12 in the transverse direction) of the nerve 12 along which the contacts 20-1, 20-2, 20-3, . . . 20-N are arranged. Amplifying only those signals induced in the contacts 20-1, 20-2, 20-3, . . . 20-N that exceed any baseline signals induced in the reference contact 32 by a predetermined magnitude can limit the noise introduced to the manipulated signal to be transmitted to the external receiver.

Each intersection (such as the intersections referred to at 34) between a border of the processor 24 in FIG. 4 and another line schematically represents an electrical connection to a terminal such as the input terminals 22 of the processor 24. Likewise, each intersection between the wires 18 and the border of the processor 24 in FIG. 4 represent an electrical connection to other terminals of the processor 24. For instance, the intersection 36 can be a single pin, surface mount pad or other suitable connector to which one of the wires 18 can be electrically connected for conducting the manipulated signal from the implanted electrode 10 to the external receiver. Similarly, the intersections 38 can represent power and ground terminals for supplying a DC or other suitable power signal to facilitate operation of the processor 24 and other components provided to the control unit 26. And the intersection 40 can represent a control terminal for inputting or otherwise communicating control signals governing operation of a multiplexer 42 or other component of the processor 24 responsible for manipulation of the signals received by the processor from the contacts 20-1, 20-2, 20-3, . . . 20-N.

One example of the signal manipulation that can be performed by the processor 24 for transmitting the signals from the electrode 10 via a shared communication channel is multiplexing. Referring once again to the embodiment shown in FIG. 4, the signals induced in the contacts 20-1, 20-2, 20-3, . . . 20-N that are adjacent to the regions 14 of the nerve 12 where electrical activity has occurred is delivered, via the insulated wires 28, to respective input terminals 22 of the process 24. The signal received at each input terminal 22 relative to a baseline signal input induced in the reference contact 32 is amplified by an amplification stage 44 electrically connected to each input terminal 22.

The amplified signals from the plurality of different contacts 20-1, 20-2, 20-3, . . . 20-N is received by a multiplexer 42 of the processor 24, which combines the information represented by the signals received from the plurality of different contacts 20-1, 20-2, 20-3, . . . 20-N into a single, multiplexed signal, in vivo. The embodiment shown in FIG. 4 is a N-to-1 analog multiplexer 42, meaning that a single multiplexer 42 is capable of manipulating analog signals received by all of the contacts 20-1, 20-2, 20-3, . . . 20-N. An example of a processor 24 provided with a suitable multiplexing component is the RHA2000 series multi-channel bioamplifier chip (e.g., RHA2116) offered by Intan Technologies LLC. However, alternate embodiments can include a plurality of multiplexers 42 to distribute the multiplexing load, where each such multiplexer 42 multiplexes fewer than all of the signals from all of the contacts 20-1, 20-2, 20-3, . . . 20-N. For such embodiments, there may be a plurality of shared communication channels over which multiplexed signals are transmitted to one or more external receivers. Further, the multiplexer 42 can optionally multiplex digital signals rather than analog signals without departing from the scope of the present disclosure. Once the signals from the contacts 20-1, 20-2, 20-3, . . . 20-N have been multiplexed, the multiplexed signal is then transmitted from the electrode 10 over the single wire 18 in the embodiment of FIG. 4 from the residual limb where the electrode is implanted to be received by the external receiver. At the external receiver, the multiplexed signals is demultiplexed and interpreted for controlling the prosthetic device, for example.

Although only a single wire 18 is used as the shared communication channel in the embodiment of FIG. 4, the number of shared communication channels over which multiplexed signals are output to the external receiver(s) can be any number less than the number of contacts 20-1, 20-2, 20-3, . . . 20-N. For instance, a ratio of at least four (4) contacts to every shared communication channel, or optionally at least sixteen (16) contacts to every shared communication channel, can be established. Sharing a communication channel reduces that number of wires, for example, that would otherwise be required to establish a dedicated communication channel for each contact 20-1, 20-2, 20-3, . . . 20-N, to output each respective signal separately. Sharing at least one communication channel reduces the forces urging separation of the electrode 10 from the nerve 12 that would otherwise be imparted by providing a dedicated communication channel for each of the 20-1, 20-2, 20-3, . . . 20-N. Thus, regardless of the number of multiplexers 42, there are fewer communication channels utilized for transmitting multiplexed signals to an external receiver than contacts 20-1, 20-2, 20-3, . . . 20-N sensing electrical activity in the nerve 12. So for the embodiment shown in FIG. 4, a total of four (4) wires 18: DC power supply, ground, control and the single shared communication channel can extend from the electrode 10 and the residual limb where the electrode 10 is implanted.

Although the detailed description of the signal manipulation herein is focused on multiplexing the received signals to be transmitted over the shared communication channel, any technique of adapting signals for transmission over a shared communication channel can be used. For instance, introducing a delay to one or more signals to allow each separate signal to be transmitted serially over the shared communication channel can be utilized instead of multiplexing.

The multiplexer 42 can optionally output the manipulated signal for transmission to the external receiver in analog form or, alternately, as a digital signal. For embodiments where the manipulated signal is transmitted from within the residual limb or other location where the electrode 10 is implanted as a digital signal, the control unit 26 can also optionally include an analog-to-digital converter ("ADC") 45 to convert the analog signal into a digital signal. As shown in FIG. 4, the ADC 45 is arranged to convert the manipulated signal output by the multiplexer 42. The digital signal from the ADC 45 is then output via a single wire 18B, for example, which is operable as the shared communication channel of the present embodiment to be conveyed to the external receiver.

Although the embodiment shown in FIG. 4 includes an ADC 45 that converts the manipulated signal output by the multiplexer 42 into a digital signal, it is to be understood that the ADC 45 can be operatively arranged at any desired location between the contacts 20-1, 20-2, 20-3, . . . 20-N and the shared communication channel that transmits the manipulated signal from the residual limb or other location where the electrode 10 is implanted. For instance, the ADC 45 can be operatively disposed to convert analog signals from the contacts 20-1, 20-2, 20-3, . . . 20-N into digital signals before the digital signals are manipulated by the multiplexer 42. For such embodiments, an ADC 45 can optionally be dedicated to convert the signals introduced to each respective contact 20-1, 20-2, 20-3, . . . 20-N.

Figure 7:
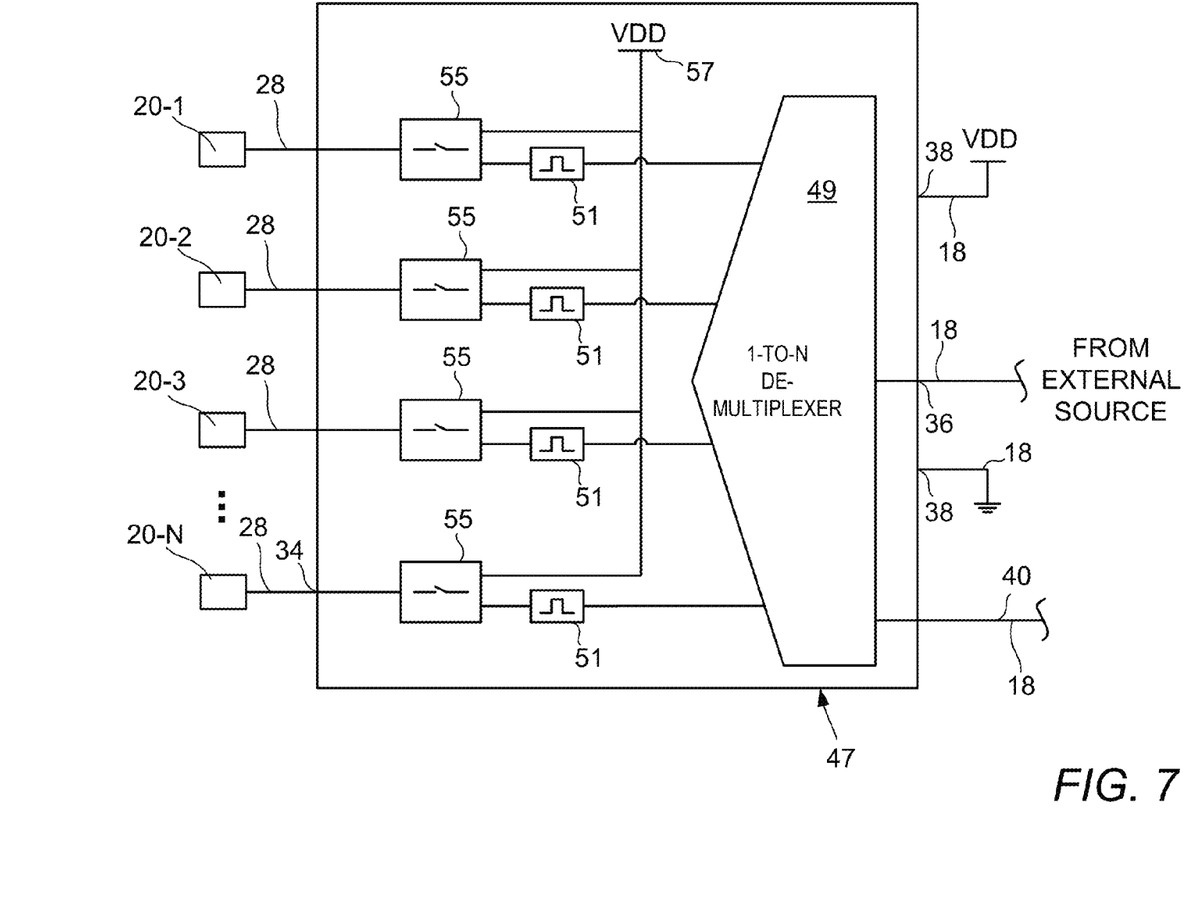
FIG. 7 shows an illustrative embodiment of a stimulator for controlling introduction of an external stimulation to a nerve.

The control unit 26 can optionally also include a stimulator 47, an embodiment of which is schematically depicted in FIG. 7. The stimulator 47, or portions thereof, can optionally be integrated as part of the processor 24, and can optionally include hardware components and/or computer-executable instructions also utilized to convey the signals introduced to the contacts 20-1, 20-2, 20-3, . . . 20-N over the shared communication channel. Regardless of its configuration, the stimulator 47 receives an instruction transmitted by the external receiver or other stimulation controller to deliver an electric signal to one or more regions 14 of the nerve 12 via respective contacts 20-1, 20-2, 20-3, . . . 20-N arranged adjacent to those regions 14 targeted. Introducing the electrical signals from the stimulator 47 via the contacts 20-1, 20-2, 20-3, . . . 20-N to the respective regions 14 of the nerve 12 can simulate a sensory perception such as touch via the nerve 12 that would otherwise require a sensory signal transmitted by an amputated limb, for example.

To explain operation of the stimulator 47, an illustrative example will be described as receiving a sensory signal indicative of a touch sensed by a prosthetic device, and delivering electrical stimulation to the regions 14 of the nerve 12 that would otherwise be stimulated by a limb replaced by the prosthetic device. However, it is understood that other external sources such as signal generators, etc. . . . can be the source of the instruction to electrically stimulate one or more of the regions 14 of the nerve 12. Additionally, the electrical stimulation is not necessarily performed to simulate a sensory perception, but can be performed as part of a therapeutic or other treatment involving nerve stimulation.

As shown in FIG. 7, the demultiplexer 49 receives the instruction signal, which is indicative of the contact sensed by the prosthetic device as the external source, via the single wire 18 or other shared communication channel. The instruction encodes at least one of: the identity of the one or more of the contacts 20-1, 20-2, 20-3, . . . 20-N that are to conduct the stimulation signal to the respective nerve regions 14 of the nerve 12, the shape of the stimulation signal to be conducted by the selected contacts 20-1, 20-2, 20-3, . . . 20-N, a power of the stimulation signal to be conducted, a timing of the stimulation signal to be delivered to the nerve 12 via each selected contact 20-1, 20-2, 20-3, . . . 20-N, and a notification that external stimulation of the nerve 12 (or another nerve as described below) is being performed to mitigate the effect of such stimulation on the signals introduced to the contacts 20-1, 20-2, 20-3, . . . 20-N that are to be manipulated as described above by the electrode 10.

The demultiplexer 49 interprets the instruction signal and identifies the contacts 20-1, 20-2, 20-3, . . . 20-N through which the stimulation signal is to be delivered to the nerve 12. The demultiplexer 49, in turn, transmits the information indicative of the signal to a waveform component 51 that can optionally be included to establish a desired waveform of the stimulation signal to be delivered to the nerve 12 through a respective contact 20-1, 20-2, 20-3, . . . 20-N. The waveform component 51 can include circuitry or other hardware and optionally embedded or other computer-executable instructions that, when executed, allow the waveform component 51 to govern operation of a respective switching component 55 to selectively connect the contacts 20-1, 20-2, 20-3, . . . 20-N to a power supply 57 ($V_{DD}$ in the present example) and generate the desired waveform.

Each switching component 55 can include a solid-state, electronically-actuated switch such as a transistor or other device operable to selectively open and close a conductive pathway between the contacts 20-1, 20-2, 20-3, . . . 20-N and the power supply 57. Although the power supply 57 is shown in the present example as the voltage $V_{DD}$ input via the wire 18 for powering the processor 24, alternate embodiments of the power supply 57 can include an on-board power supply such as a rechargeable battery provided to the control unit 26. Regardless of the nature of the power supply 57, the power supply 57 can supply a suitable electric current and voltage to effectively stimulate the regions 14 of the nerve 12.

As mentioned above, the instruction signal received by the demultiplexer 49 can include a notification that external stimulation of the nerve 12 (or another nerve) is being performed. Since the contacts 20-1, 20-2, 20-3, . . . 20-N are also used for sensing electrical activity in the nerve 12 to be transmitted externally, it is conceivable that artifacts or other noise resulting from the external stimulation of the nerve 12 could be introduced to the contacts 20-1, 20-2, 20-3, . . . 20-N that are not involved in the external stimulation. Such contacts 20-1, 20-2, 20-3, . . . 20-N that are not involved in an external stimulation of the nerve 12 by the electrode are referred to hereinafter as "inactive contacts". The inactive contacts may reside on the electrode 10 being used to perform the external stimulation or another electrode 10 coupled to a different nerve, or a different branch of the same nerve 12. But regardless of the electrode 10 on which they reside, the inactive contacts can optionally be isolated from portions of the processor 24 such as the multiplexer 42. According to alternate embodiments, any signals introduced to the contacts 20-1, 20-2, 20-3, . . . 20-N that are inactive contacts when an external stimulation is being performed can be excluded, or otherwise ignored to avoid affecting the manipulated signal output by the multiplexer 42 and transmitted over the shared communication channel to the external receiver. In other words, the effect of the external stimulation introduced by the electrode 10 or another electrode implanted at a location where such external stimulation affects the signals introduced to the electrode 10 can be excluded from the manipulated signal transmitted via the shared communication channel to the external receiver. Such artifacts are not indicative of signals conducted by the nerve 12 in response to a control signal from the brain, but indicative of the external stimulation, and can be excluded from consideration in generating the manipulated signal to be transmitted from the electrode 10 over the shared communication channel to the external receiver.

The notification received by the stimulator 47 can include at least one of: a time when external stimulation is to be performed, information indicative of the one or more electrodes that are to perform the external stimulation, and information that can be used to identify the inactive contacts. For embodiments where the inactive contacts are electrically isolated from other circuit components, the respective switching component 55 of each inactive contact can be operable to isolate the respective contacts 20-1, 20-2, 20-3, . . . 20-N from the multiplexer 42 in addition to selectively conducting the stimulation signal to the contacts 20-1, 20-2, 20-3, . . . 20-N. Each switching component 55 provided to an electrode 10 that is to perform external stimulation of the nerve 12 can be adjusted to a state that isolates the contacts 20-1, 20-2, 20-3, . . . 20-N from the multiplexer 42 during performance of the external stimulation to avoid conducting artifacts resulting from external stimulation to the multiplexer 42.

According to alternate embodiments, the control unit 26 of the electrode 10 can optionally receive information indicating that external stimulation of the nerve 12 is to be performed by another electrode that can affect the electrical activity along that nerve 12. For example, external stimulation is to be performed using an electrode provided to a trunk region of the nervous system from which the nerve 12 is branched. Such information can also optionally include timing information that allows the control unit 26 that received the information to isolate the contacts 20-1, 20-2, 20-3, . . . 20-N or otherwise exclude from consideration in generating the manipulated signal any signals introduced to the contacts 20-1, 20-2, 20-3, . . . 20-N when such external stimulation occurs.

Figure 5:
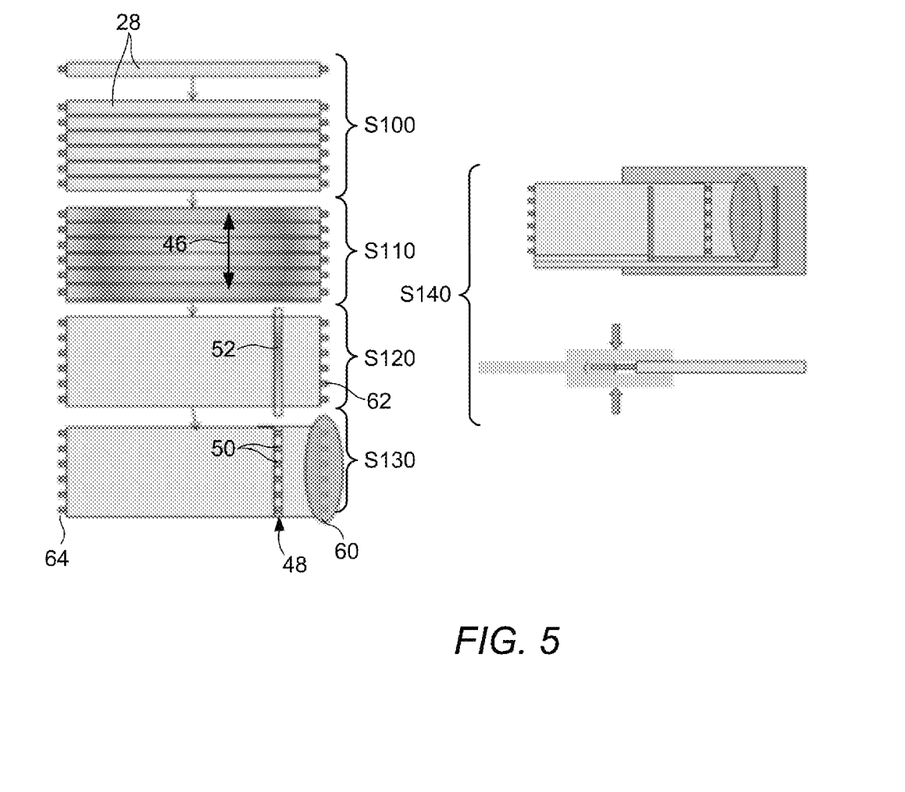
FIG. 5 shows steps of an illustrative embodiment of a method of forming an electrode.
Figure 6:
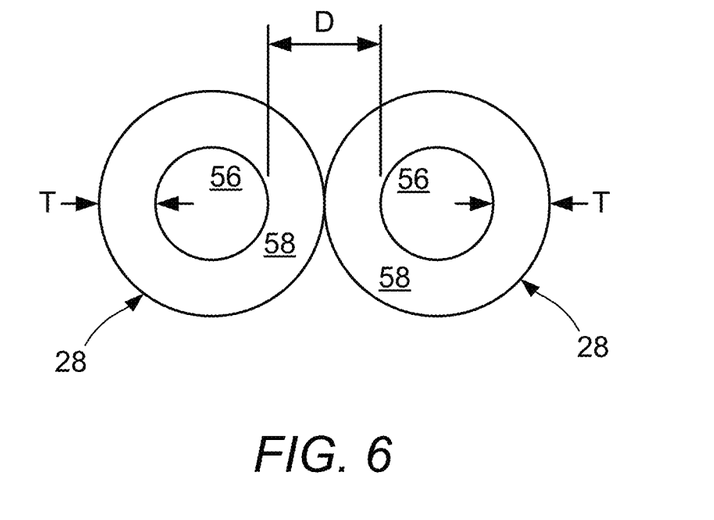
FIG. 6 shows an end view of immediately-adjacent insulated wires arranged to be formed into an array of contacts.

A method of fabricating the electrode 10 can be understood with reference to FIG. 5. Each contact 20 and wire 28 establishing the conductive pathway between the contacts 20 and the processor 24 can be formed from a single segment of an electrically conductive material, such as printed conductors, thin films of a conductive material, and stranded, and optionally braided stainless steel conductor 56, shown in the end view of immediately-adjacent wires 28 in FIG. 6, coated in Polytetrafluoroethylene ("PTFE"), for example, or other suitable electrically insulating material 58. A plurality of such wires 28, corresponding to the number of contacts 20 needed, are arranged and optionally tightly packed side by side (i.e., parallel with each other) in a single row at step S100 in FIG. 5. Arranging the wires 28 so they are touching each other in such a parallel orientation limits the distance D, shown in FIG. 6, separating the stranded conductor 56 in immediately adjacent (i.e., touching) wires 28 to a distance D equal to twice the thickness T of the insulating material 58 protecting the stranded conductors 56 of those wires 28. And since the thickness T of the insulating material of each wire 28 is approximately the same, even if the wires 28 are arranged by hand instead of by an automated machine, substantially equal spacing of the neighboring stranded conductors 56 (and resulting contacts 20) can be achieved.

At step S110 in FIG. 5, a suitable amount of heat is applied to fuse the insulating material 58 of the immediately-adjacent wires 28 together. Fusing the insulating material 58 maintains the relative arrangement of each of the wires 28 but allows a degree of flexibility to bend about an axis extending in the transverse direction, indicated by arrow 46 in FIG. 5, of the wires 28.

A heated filament, hot knife or other suitable stripping device 52 can then be used at step S120 to strip a portion of the insulating material from each wire 28 to form an aperture 48 in the insulating material 58 provided to each of the wires 28. A portion 50 of each stranded conductor 56 is exposed as a result, and forms the contact 20 for each respective wire 28 in which a signal is to be induced by electrical activity in the nerve 12. Each resulting contact 20 can optionally be aligned in the transverse direction 46, perpendicular to a longitudinal axis of the wires 28, and the plurality of contacts 20 can extend entirely across the arrangement of wires 28. A silicone-based sealant or other suitable electrical insulator 60 can be applied at step S130 to a terminal end 62 of the plurality of insulated wires 28 adjacent to the aperture 48 formed in the insulating material 58. The opposite end 64 of the stranded conductors 56 can be electrically connected to the input terminals 22 of the processor 24 for delivering the signals induced in the contacts 20 to the processor 24 to be manipulated.

Depending on the use, this array of contacts 20 can be received in a housing 62 forming the cuff 16 to be implanted. According to one example, a sheet of silicone with a polyimide stiffener was arranged to sandwich the array of contacts 20 there between at step S140. The silicon sheets can be sealed together about the array of wires 28 using an adhesive. According to alternate embodiments, the array of wires 28 can optionally be included in an injection molder and the silicon injection molded about the array.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An electrode for monitoring electrical activity of a nerve, the electrode comprising:
   a cuff formed from a chronically-implantable material and configured to extend at least partially around an external periphery of the nerve when implanted;
   a plurality of insulated wires fully encased within the cuff, each including a stranded conductor surrounded by an insulator, wherein a portion of the insulator is
   removed on each of the plurality of insulated wires to reveal a portion of the stranded
   conductor to form a contact, wherein each of the plurality of contacts is arranged to be adjacent different regions of the external periphery in a transverse direction of the nerve when the cuff is implanted;
   an implantable control unit comprising a multiplexer is operatively connected to the plurality of contacts by the plurality of insulated wires to receive electrical signals introduced to at least one of the plurality of contacts by the nerve at least one of the different regions, said multiplexer being configured to multiplex, in vivo, the received electrical signals so that multiplexed electrical signals are transmitted to a receiver over a shared communication channel; and
   the stranded conductor of each of the plurality of insulated wires establishes a conductive path between the respective contact and the multiplexer.

2. The electrode of claim 1, wherein each stranded conductor comprises a plurality of corrosion-resistant wire filaments wound together.

3. The electrode of claim 1, wherein the implantable control unit further comprises an amplifier operatively disposed between the contacts and the multiplexer to amplify the electrical signals before the electrical signals are received by the multiplexer.

4. The electrode of claim 3, wherein the amplifier and the multiplexer are formed as portions of a common integrated circuit.

5. The electrode of claim 1, wherein the shared communication channel comprises a plurality of output terminals provided to the multiplexer, and a quantity of the output terminals included as part of the shared communication channel is less than a quantity of the contacts.

6. The electrode of claim 1, wherein the shared communication channel comprises a single output terminal provided to the multiplexer, and the electrical signals introduced to each of the contacts are all transmitted to the receiver over the single output terminal.

7. The electrode of claim 1, wherein the shared communication channel comprises a plurality of output terminals provided to the multiplexer, and the electrical signals introduced to at least four of the contacts are transmitted to the receiver over each of the plurality of output terminals.

8. The electrode of claim 1, wherein the plurality of contacts form an array comprising substantially equal spacing between each of the contacts.

9. The electrode of claim 1, wherein the implantable control unit further comprises a demultiplexer to separate a stimulation signal from a stimulator into a delivery signals corresponding to at least two of the plurality of contacts to cause delivery of the stimulation signal to a target region.

10. The electrode of claim 1, wherein the implantable control unit further comprises an analog-to-digital converter adapted to convert the electrical signals from an analog state to a digital state before the electrical signals are transmitted to the receiver over the shared communication channel.

11. The electrode of claim 10, wherein the analog-to-digital converter is operatively disposed between the multiplexer and the shared communication channel to convert a multiplexed signal output by the multiplexer into the digital state before the multiplexed electrical signal are transmitted over the shared communication channel.

* * * * *